(12) United States Patent
Choi et al.

(10) Patent No.: US 8,521,298 B2
(45) Date of Patent: Aug. 27, 2013

(54) ELECTRICAL STIMULATION METHOD AND APPARATUS TO STIMULATE NERVE FIBERS

(75) Inventors: Charles Tak-Ming Choi, Hsinchu County (TW); Yi-Hsuan Lee, Taichung (TW)

(73) Assignee: National Chiao Tung University, Hsinchu (TW)

( * ) Notice: Subject to any disclaimer, the term of this patent is extended or adjusted under 35 U.S.C. 154(b) by 101 days.

(21) Appl. No.: 12/987,897

(22) Filed: Jan. 10, 2011

(65) Prior Publication Data

US 2011/0230933 A1    Sep. 22, 2011

(30) Foreign Application Priority Data

Mar. 17, 2010  (TW) ................. 99107905 A

(51) Int. Cl.
*A61N 1/00*     (2006.01)
*A61N 1/36*     (2006.01)
(52) U.S. Cl.
USPC .................. 607/57; 607/55; 607/56; 607/137
(58) Field of Classification Search
USPC ........................................ 607/55, 56, 57, 137
See application file for complete search history.

(56) References Cited

U.S. PATENT DOCUMENTS

| | | | | |
|---|---|---|---|---|
| 4,532,930 A | * | 8/1985 | Crosby et al. | 607/57 |
| 7,421,298 B2 | * | 9/2008 | Daly et al. | 607/57 |
| 7,515,966 B1 | * | 4/2009 | Litvak et al. | 607/57 |

* cited by examiner

*Primary Examiner* — Thomas J Sweet
*Assistant Examiner* — Krutanjali M Shah
(74) *Attorney, Agent, or Firm* — WPAT, P.C.; Anthony King

(57) ABSTRACT

The present invention provides an electrical stimulation method and apparatus to stimulate nerve fibers, turning on suitable combination of adjacent electrodes simultaneously to form virtual channels based on predetermined rules, so that the stimulation signal will generate or evoke a nerve response spectrum that matches the original signal spectrum presented as the input sound. The method includes the steps of receiving a sound signal by a receiving unit; dividing the received sound signal into a plurality of frequency bands by a processing unit; extracting a spectral peak from each of the frequency bands and determining a stimulation sequence of frequency bands by the processing unit; and selectively driving a plurality of electrode groups in a plurality of cycles based on the stimulation sequence of frequency bands and a determination rule by the processing unit, so that the nerve response that matches the original signal will be generated.

18 Claims, 8 Drawing Sheets

```
HiRes120
                  8
cycle  1    | 0  1 |  2  3  4  5  6  7  8  9  10  11  12  13  14  15
                                11
cycle  2    0  1  2  3  4  | 5  6 |  7  8  9  10  11  12  13  14  15
                                              12
cycle  3    0  1  2  3  4  5  6  7  8  9  | 10  11 |  12  13  14  15
                  9
cycle  4    0  | 1  2 |  3  4  5  6  7  8  9  10  11  12  13  14  15
                              2
cycle  5    0  1  2  3  4  5  | 6  7 |  8  9  10  11  12  13  14  15
                                              13
cycle  6    0  1  2  3  4  5  6  7  8  9  10  | 11  12 |  13  14  15
                      4
cycle  7    0  1  | 2  3 |  4  5  6  7  8  9  10  11  12  13  14  15
                                  3
cycle  8    0  1  2  3  4  5  6  | 7  8 |  9  10  11  12  13  14  15
                                                    5
cycle  9    0  1  2  3  4  5  6  7  8  9  10  11  | 12  13 |  14  15
                          1
cycle 10    0  1  2  | 3  4 |  5  6  7  8  9  10  11  12  13  14  15
                                        14
cycle 11    0  1  2  3  4  5  6  7  | 8  9 |  10  11  12  13  14  15
                                                        10
cycle 12    0  1  2  3  4  5  6  7  8  9  10  11  12  | 13  14 |  15
                              6
cycle 13    0  1  2  3  | 4  5 |  6  7  8  9  10  11  12  13  14  15
                                            7
cycle 14    0  1  2  3  4  5  6  7  8  | 9  10 |  11  12  13  14  15
                                                              15
cycle 15    0  1  2  3  4  5  6  7  8  9  10  11  12  13  | 14  15 |
```

ELECTRICAL STIMULATION METHOD AND APPARATUS TO STIMULATE NERVE FIBERS

FIELD OF THE INVENTION

The present invention relates to an electrical stimulation method and apparatus thereof, and more particularly to a hybrid technique of using multiple electrode groups to generate multiple stimulation signals through current steering.

BACKGROUND OF THE INVENTION

Currently, neural stimulation has been widely applied in neural prosthesis. For example, the cochlear implant allows a patient to perceive sounds of different frequencies by generating electronic signals to stimulate the patient's auditory nerves; and the artificial retina allows a patient to have visual perception by generating electric stimulation to the patient's retina or visual cortex. Since the number of electrodes that can be provided with the neural prosthesis is limited and much less than the quantity of the human nerves, there is a relatively large difference between the sound perceived through electrical stimulation signals and the sound perceived through normal hearing persons. For the patients to have better and improved perception, it is very important to establish a proper stimulation strategy, so that the stimulation signals can generate a perception that is closely match the perception generated by the original sound signals.

Taking the cochlear implant as an example, when the electrodes have been implanted in the patient's cochlea, each of the implanted electrodes corresponds to a center frequency. That is, when one of the electrodes is turned on, the patient would perceive a sound signal having a specific frequency, and this process is referred to as forming a fixed channel. Currently, there are three most common electrical stimulation strategies. In the first electrical stimulation strategy, for example the ACE strategy proposed by Cochlear, an Australian company, the sound signal is decomposed to twenty-two frequency bands, and twenty-two electrodes are provided for simulating the twenty-two frequency bands respectively. In other words, each of the frequency bands corresponds to one electrode, and each of the electrodes is used to provide a fixed channel with a specific frequency. Then, 8-16 frequency bands having the higher energy values are selected, and the 8-16 corresponding electrodes are turning on in one single cycle. The electric current is input to these electrodes to generate electrode stimulation signals. In the second electrical stimulation strategy, the sound signal is also decomposed to several frequency bands, and each of the bands corresponds to one electrode. An energy value is extracted from each of the bands, and the electrodes separately corresponding to different bands are sequentially turned on in different cycles. That is, the electrodes are sequentially turned on in continuous cycles to present signals of all bands.

In the above two electrical stimulation strategies, fixed channels are used to synthesize the original sound signal, which means the simulated sound signals perceived by the patient are synthesized by fixed frequency components. However, as shown in FIG. 1, to more accurately reproduce the original sound signal spectrum, it is necessary to select the frequencies with the highest energy values for synthesizing the sound signal. That is, in the use of fixed channels to synthesize the original sound signal spectrum, it is possible the frequencies with the highest energy values in the original sound signal fall out of the range of the center frequencies of the electrodes. As a result, there would be a relatively large difference between the stimulating signal spectrum and the original sound signal spectrum.

In the third electrical stimulation strategy, a stimulation signal having a frequency ranged between the center frequencies of two adjacent electrodes is generated by turning on the two adjacent electrodes at the same time through current steering, and this process is referred to as forming a virtual channel. With current steering, the frequencies with higher energy values in the original sound signal can be generated. With the third electrical stimulation strategy, the stimulation sound signal spectrum and its peaks resemble the original sound signal spectrum better, as can be seen in FIG. 1. According to the third electrical stimulation strategy, the sound signal spectrum is first divided into several frequency bands, and the energy value of each of the bands is obtained in order to locate the frequencies corresponding to the highest energy values in all bands. Then, in each of several continuous cycles, two adjacent electrodes are simultaneously turned on, so as to create a frequency corresponding to the highest energy value in the band corresponding to the two adjacent electrodes and generate a stimulation signal for the band. By sequentially turning on different pairs of two adjacent electrodes in continuous cycles to obtain stimulation signals for all bands, stimulation sound signal spectrums which closely approximate the original sound signal spectrums can be generated.

Please refer to FIG. 2 that shows the third electrical stimulation strategy according to prior art. As shown, according to the prior art third electrical stimulation strategy, a sound signal received by a microphone is first divided into a plurality of frequency bands, such as 15 bands. Then, the highest energy value, or a spectral peak, of each of the bands and the frequency corresponding thereto are obtained. That is, 15 frequencies and 15 spectral peaks thereof that are to be generated. And, total 15 groups of two adjacent electrodes separately corresponding to the 15 bands are turned on in a fixed sequence in 15 continuous cycles. In FIG. 2, the groups of two adjacent electrodes are turned on in the sequence of 8, 11, 12, 9, 2, 13 . . . , 6, 7 and 15 in fifteen cycles. The amount of electric current supplied to each of the electrodes is decided according to the amplitude of the spectral peak of the band, so as to generate the sound signal as received by the microphone.

The neural stimulation techniques using the above three electrical stimulation strategies still have the problems of poor electrode utilization efficiency and large discrepancy between the original sound signal spectrum and the stimulation sound signal spectrum as perceived by the patient.

SUMMARY OF THE INVENTION

The primary object of the present invention is to provide an electrical stimulation method and apparatus to stimulate nerve fibers, according to which combination of adjacent electrodes are turned on simultaneously to form a virtual channel, so that the stimulation signal will generate or evoke a nerve response spectrum that matches the original signal spectrum presented as the input sound. Another object of the present invention is to provide an electrical stimulation method and apparatus to stimulate nerve fibers, to which a processing unit drives non-fixed number of electrodes in each cycle to increase the utilization efficiency of electrodes and further decrease the number of cycles.

To achieve the above and other objects, the electrical stimulation method to stimulate nerve fibers according to the present invention includes the follow steps of receiving a sound signal by a receiving unit; dividing the received sound signal into a plurality of frequency bands by a processing unit;

extracting a spectral peak from each of the frequency bands and determining a stimulation sequence of each frequency bands based on the energy values of spectral peaks by the processing unit; selectively driving a plurality of electrode groups in a plurality of cycles based on the stimulation sequence of each frequency bands and a determination rule by the processing unit, so that a plurality of stimulation signals corresponding to each of the frequency bands are generated; and finally, presenting the sound signal through the plurality of stimulation signals. In the present invention, the determination rules include disposing at least one electrode between each of the electrode groups (which avoid spatial interaction between electrode groups), avoiding the electrode driven in the continuous cycles (avoid temporal interaction between electrode groups), or avoiding the electrode groups in two adjacent ones of the plural cycles from repeatedly using the same electrodes (avoid temporal interaction between electrode groups).

To achieve the above and other objects, the electrical stimulation apparatus to stimulate nerve fibers according to the present invention includes a micro-electrode array, a receiving unit, and a processing unit. The micro-electrode array includes a plurality of electrodes, and the electrodes respectively correspond to a different center frequency after the electrodes are driven. The receiving unit receives a sound signal. The processing unit divides the received sound signal into a plurality of frequency bands, extracts a spectral peak from each of the frequency bands, and determines a stimulation sequence of each frequency bands based on the energy values of the spectral peaks. The processing unit also selectively drives a plurality of electrode groups in a plurality of cycles based on the stimulation sequence of each frequency bands and a determination rule, so that a plurality of stimulation signals corresponding to each of the frequency bands are generated and the sound signal is presented through the plurality of stimulation signals. The determination rules include disposing at least one electrode between each of the electrode groups (which avoid spatial interaction between electrode groups), avoiding the electrode driven in the continuous cycles (avoid temporal interaction between electrode groups), or avoiding the electrode groups in two adjacent ones of the plural cycles from repeatedly using the same electrodes (avoid temporal interaction between electrode groups).

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
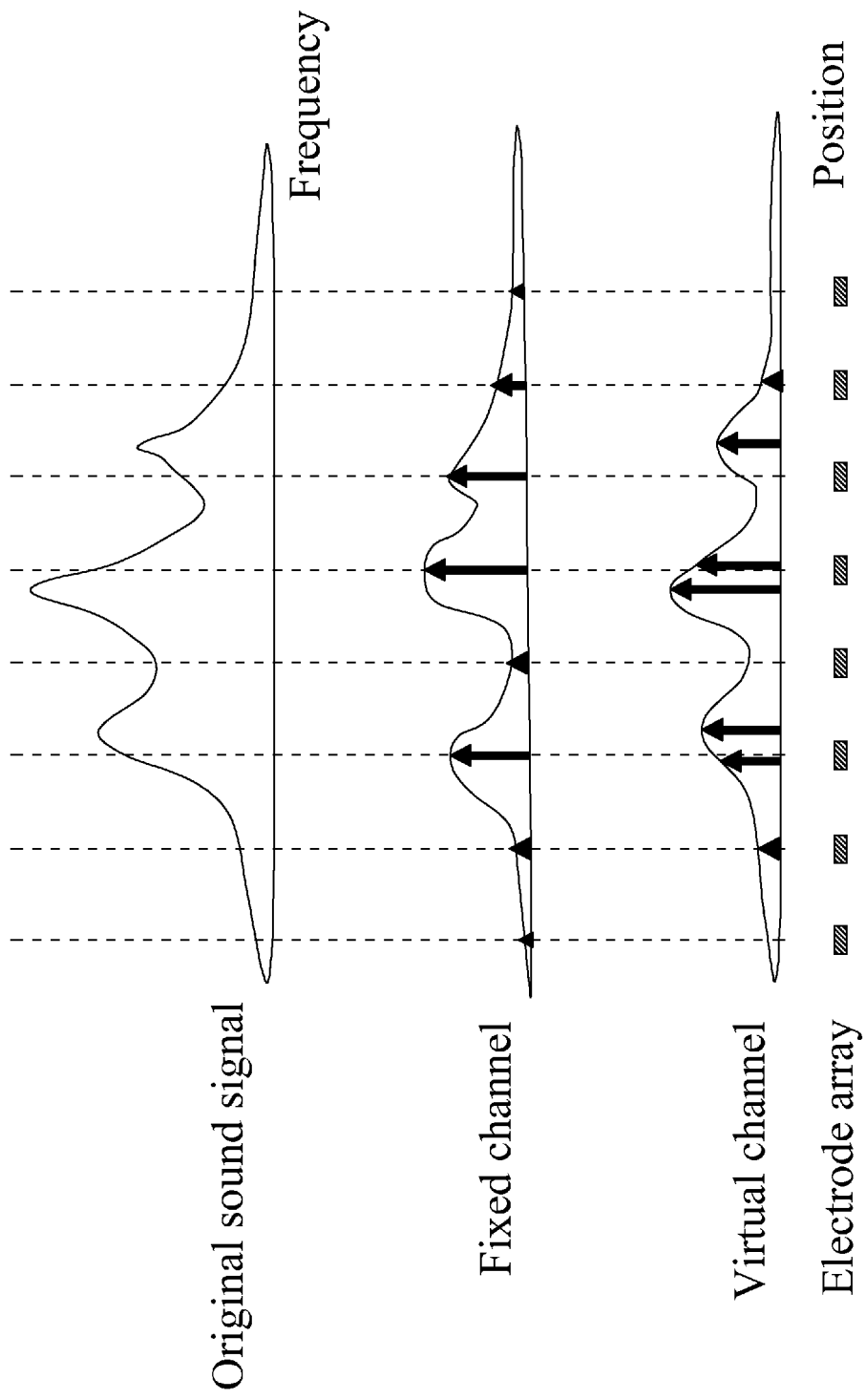
FIG. 1 shows the synthesis of an original sound signal separately using fixed channels and virtual channels.
Figure 2:
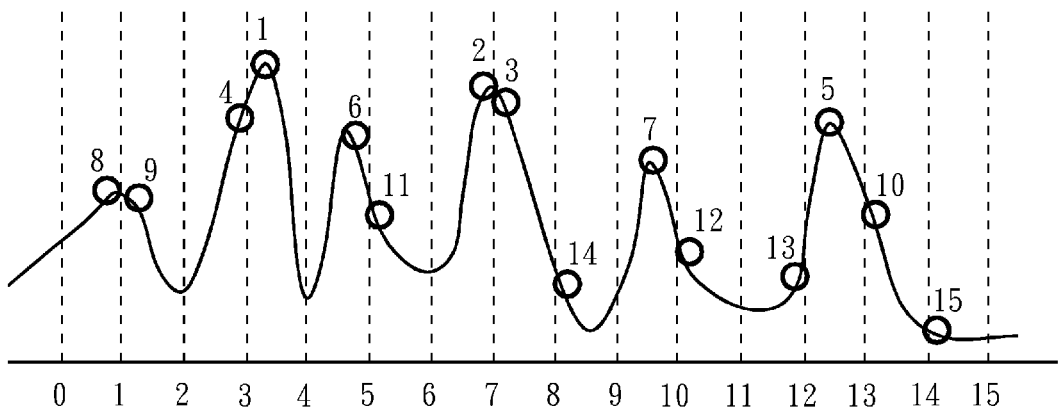
FIG. 2 shows a third type of electrical stimulation strategy in prior art.
Figure 3:
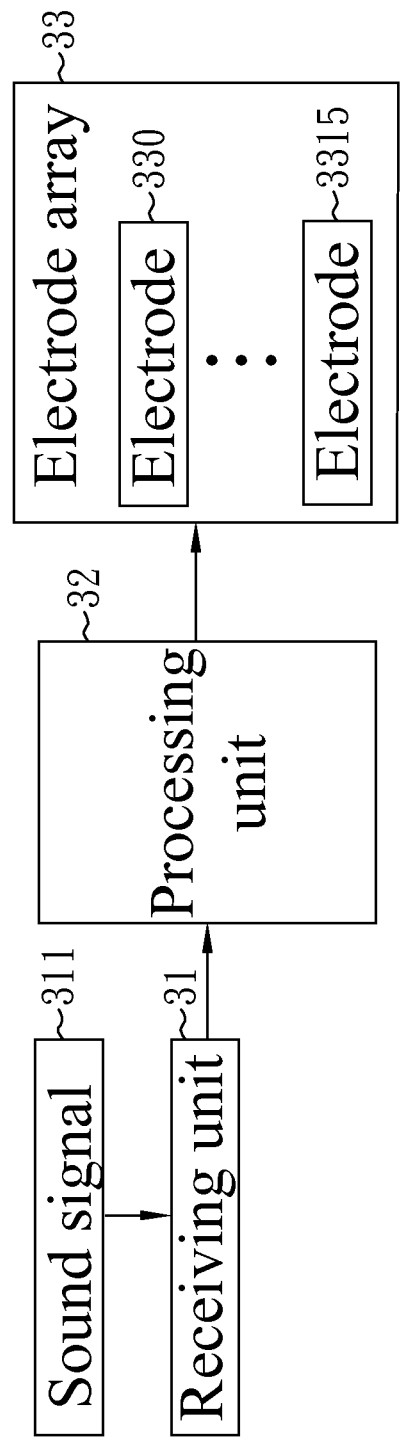
FIG. 3 is a block diagram of an electrical stimulation apparatus to stimulate nerve fibers according to a preferred embodiment of the present invention.
Figure 4:
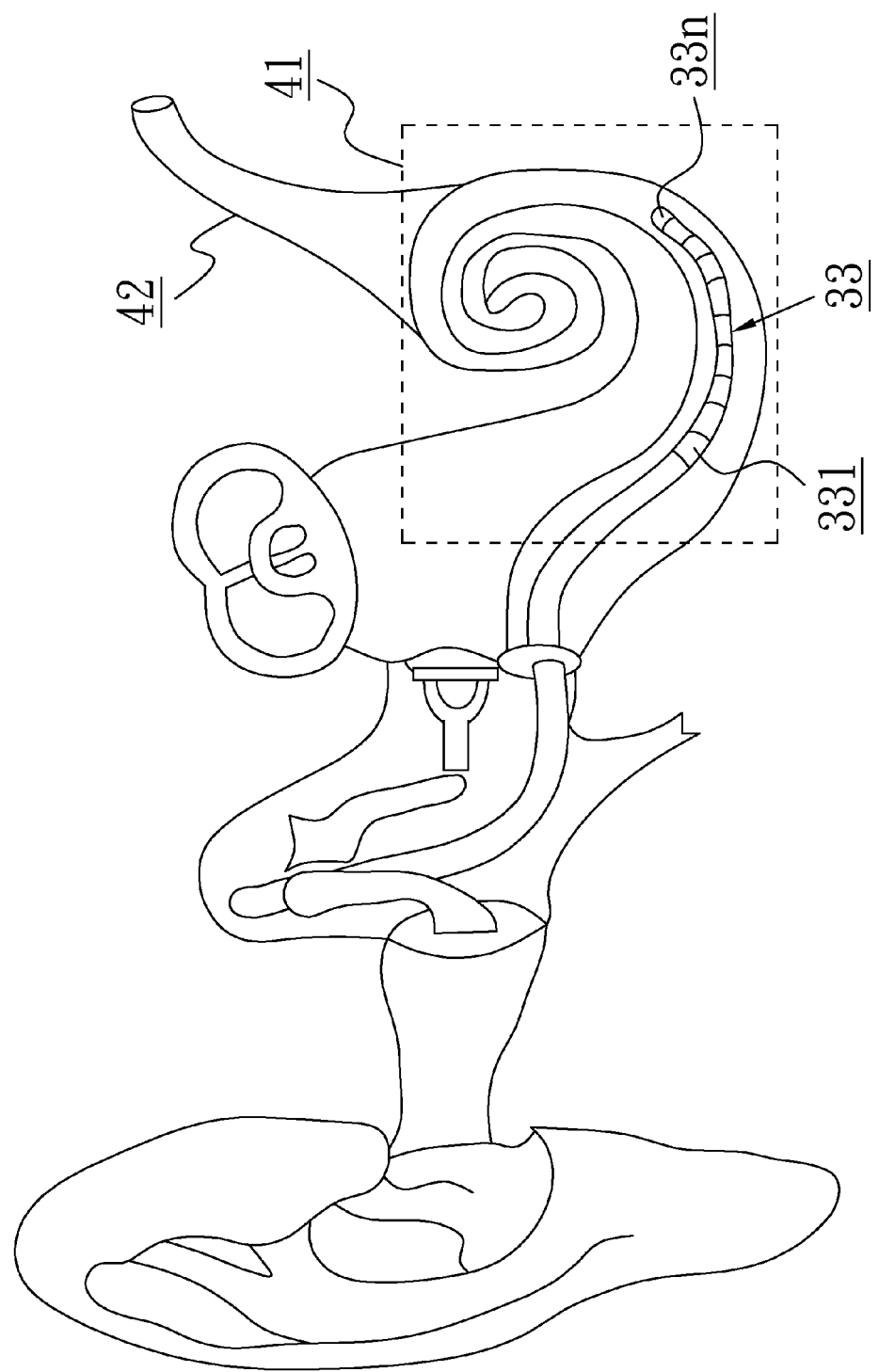
FIG. 4 shows an electrode array according to the present invention being implanted in a cochlea.

Please refer to FIG. 3 that is a block diagram of an electrical stimulation apparatus to stimulate nerve fibers according to a preferred embodiment of the present invention. As shown, the electrical stimulation apparatus 3 includes a receiving unit 31, a processing unit 32, and an electrode array 33. The receiving unit 31 can be a microphone for receiving a sound signal 311. The processing unit 32 can include a band-pass filter for dividing the sound signal 311 into a plurality of frequency bands. Alternatively, the processing unit 32 can divide the sound signal 311 into a plurality of frequency bands through Fast Fourier Transform (FFT) or other spectrum computation method. After the sound signal 311 received by the microphone is analyzed by the processing unit 32, a relationship between frequency and energy intensity can be obtained. The electrode array 33 is implanted in a patient's body. When the electrical stimulation apparatus is applied to a cochlear implant, the electrode array 33 is implanted in a patient's cochlea 41, as shown in FIG. 4. Electrodes in the electrode array 33 are separately used to stimulate the auditory nerve 42, so that the patient can perceive sounds of different frequencies. Therefore, each of the electrodes corresponds to a center frequency. Generally speaking, due to the limited space in the cochlea 41, the number of electrodes included in the electrode array 33 is ranged between about 16 to about 22. In the following description of the preferred embodiment of the present invention, the electrode array 33 includes 16 electrodes, which are separately denoted by reference numerals 330, 331, 332 . . . 3313, 3314 and 3315.

Figure 5:
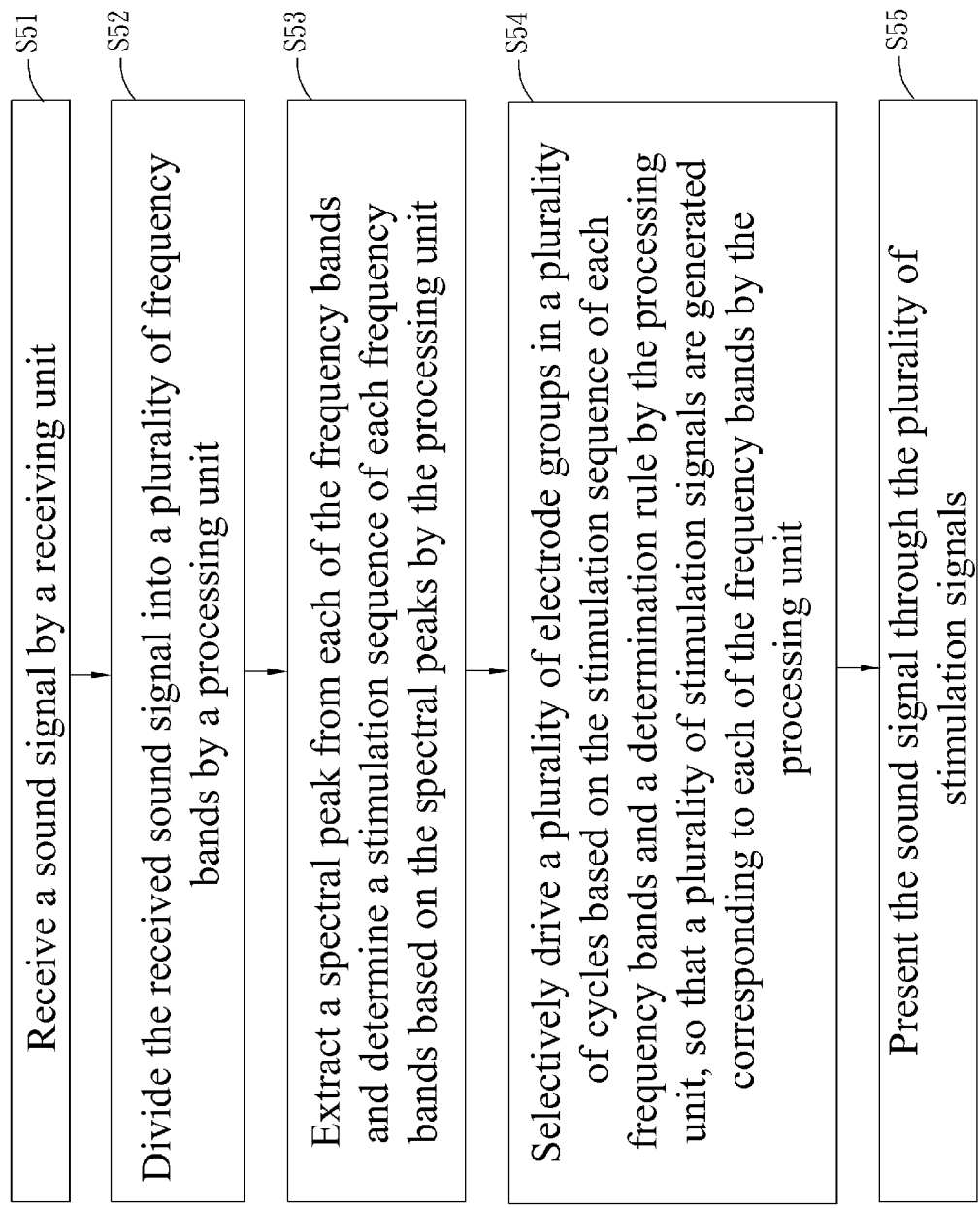
FIG. 5 is a flowchart showing the steps included in an electrical stimulation method to stimulate nerve fibers according to the present invention.

Please refer to FIG. 5 that is a flowchart showing the steps included in an electrical stimulation method to stimulate nerve fibers according to the present invention. As shown, in a step S51, a sound signal is received by a receiving unit. Then, in a step S52, the received sound signal is divided by a processing unit into a plurality of frequency bands. And, in a step S53, a spectral peak is extracted from each of the frequency bands and a stimulation sequence of each frequency bands is determined based on the energy values of spectral peaks by the processing unit. Thereafter, in a step S54, a plurality of electrode groups is selectively driven by the processing unit in each of a plurality of cycles based on the stimulation sequence of each frequency bands and a determination rule, so that a plurality of stimulation signals corresponding to each of the frequency bands are generated. Finally, in a step S55, the sound signal is presented through the plurality of stimulation signals. In the present invention, the determination rules include disposing at least one electrode between each of the electrode groups (which avoid spatial interaction between electrode groups), avoiding the electrode driven in the continuous cycles (avoid temporal interaction between electrode groups), or avoiding the electrode groups driven in two adjacent ones of the plural cycles from repeatedly using the same electrodes (avoid temporal interaction between electrode groups). Briefly speaking, the determination rule can be provided to avoid the temporal interaction and the spatial interaction between stimulation signals from different bands on the nerve fibers. Temporal and spatial interaction can reduce the performance of the apparatus. To avoid temporal interaction, the electrode $E_i$ can be turned on in cycle j, but the electrode $E_i$ can not be turned on in cycle j+1. For avoiding the spatial interaction, the electrode $E_i$ can be turned on in cycle j, but electrode $E_{i-1}$ and electrode $E_{i+1}$ can not be turned on in cycle j+1. The determination rule also can be extended to the electrode $E_{i-2}$ and electrode $E_{i+2}$.

Figure 6:
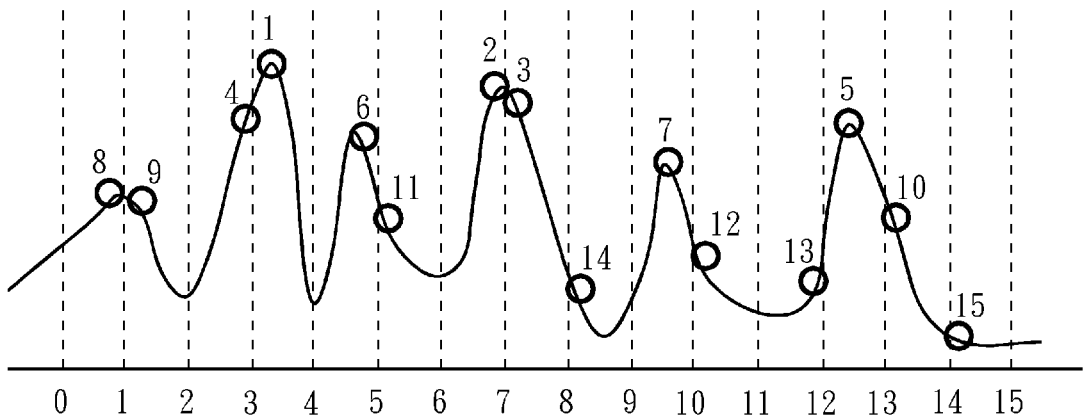
FIG. 6 shows the flow process in a first embodiment of the electrical stimulation method according to the present invention.

Please refer to FIG. 6 that shows the flow process of a first embodiment of the electrical stimulation method to stimulate nerve fibers according to the present invention. In the first embodiment, 16 electrodes are provided and denoted by 0, 1, 2 . . . , and 15, respectively. Every electrode corresponds to a center frequency. The center frequencies of any two adjacent electrodes constitute a band and therefore, total 15 bands are formed. By driving the 16 electrodes to stimulate nerve fibers, it is able to reproduce the sound signal spectrum originally received by the receiving unit, which can be a microphone. When the microphone receives the sound signal, the received sound signal is analyzed by the processing unit to obtain a corresponding relationship between frequency and energy intensity thereof. In FIG. 6, x-axis indicates the frequencies of the sound signal, and y-axis indicates the energy intensity of the sound signal. The processing unit can divide the sound signal into a plurality of frequency bands. In the illustrated first embodiment, the sound signal is divided into 15 bands. The processing unit extracts a spectral peak from each of the 15 bands (in FIG. 6, these spectral peaks are separately circled and marked from 1 to 15), so as to determine the stimulation sequence of the bands. In FIG. 6, the higher the spectral peak is, the higher the energy intensity corresponding to the frequency will be. Therefore, in the electrical stimulation apparatus and method of the present invention, the signals with higher energy intensities will be processed first, so that the user can get the most important frequency components in the sound signal.

Figure 7:
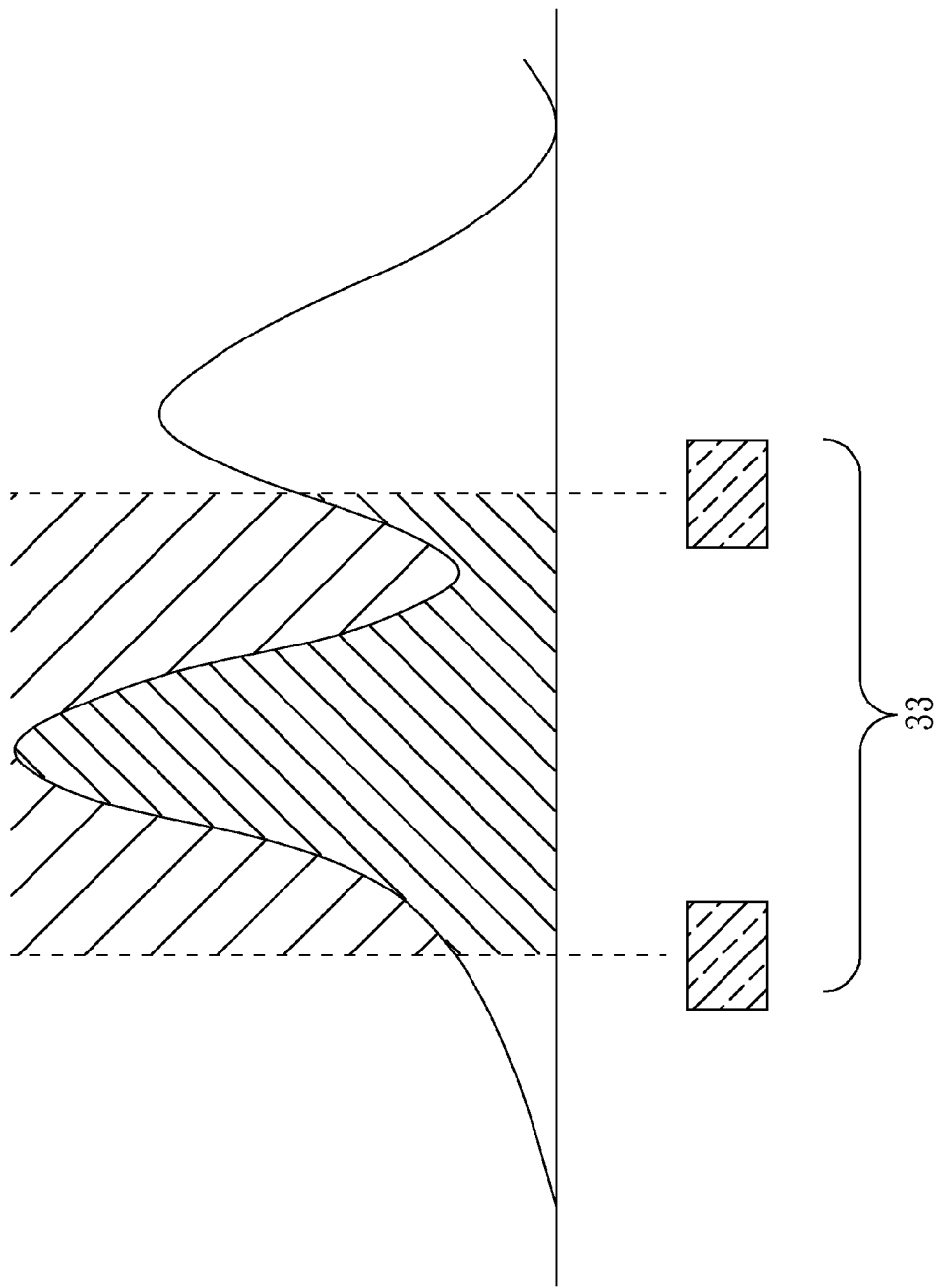
FIG. 7 explains the manner of deciding the number of electrodes to be included in one electrode group according to the present invention.

The number of electrodes to be selected can be determined in different manners. One of the selecting criteria is based on the distribution of the frequencies of the bands by comparing a rectangular area with the area covered by a waveform of the signal in each band. For example, as shown in FIG. 7, when the waveform covers an area larger than a percentage, such as 75%, of the rectangular area, it represents the band has a relatively decentralized frequency distribution. In this case, it is determined that two electrodes are suitable to be used to stimulate the auditory nerves. On the other hand, when the waveform covers an area smaller than 75% of the rectangular area, it represents the band has a relatively centralized frequency distribution. In this case, it is determined that four electrodes are to be used to stimulate the auditory nerves. The 75% is an arbitrary threshold and can be adjusted. When two electrodes are used to make the stimulation, it is able to generate a waveform with a relatively wide bandwidth; and when four electrodes are used to make the stimulation, it is able to create a waveform with a relatively narrow bandwidth. By "create a waveform with a relatively narrow bandwidth", it means the stimulated auditory nerve corresponds to a relatively small frequency range, which is more centralized at a specific frequency for the user to more clearly recognize the sound at this specific frequency.

The determination rule according to the present invention is set mainly to avoid any signal distortion of the stimulation signals in different bands due to spatial interaction effect or temporal interaction effect. The spatial interaction effect can be avoided by spacing any two selected electrode groups from each other by at least one electrode. That is, the selected electrode groups for each cycle should not adjoin to each other. For example, when the electrodes 3, 4 are selected as the first electrode group in the cycle 1, the electrodes to be selected as the second electrode group in the cycle 1 should not include the electrode 2 and the electrode 5. The temporal interaction effect can be avoided by not repeating the same electrode in the selected electrode groups in any two adjacent ones of the plural cycles. For example, when the electrodes 3 and 4 are selected as the first electrode group in the cycle 1, the electrodes to be selected as the second electrode group in the cycle 2 should not include the electrodes 2, 3, 4, 5 again. It is a must to simultaneously avoid the spatial interaction effect and the temporal interaction effect, so that the stimulation signals of different bands would not interfere with one other to cause signal distortion thereof.

Please refer to FIG. 6 that shows the flow process of a first embodiment of the electrical stimulation method to stimulate nerve fibers according to the present invention. First, eight cycles 1 to 8 are preset to present the sound signal received by the microphone, and at most two electrode groups are arranged in each of the cycles. However, it is understood the number of cycles according to the present invention is not necessarily limited to eight, and the number of the electrode groups in each cycle is not necessarily limited to two in other embodiments. Since the band having the spectral peak marked by the circle 1 has the largest energy value, the processing unit arranges the first electrode group (3, 4) in the cycle 1 to generate a stimulation signal corresponding to this band. Since the waveform in this band covers an area larger than a preset percentage, two electrodes 3, 4 are selected as the first electrode group to stimulate the nerve fibers.

Then, the processing unit arranges to generate a stimulation signal corresponding to the band having the spectral peak marked by the circle 2. Since the waveform in this band covers an area smaller than a preset percentage, four electrodes 5, 6, 7, and 8 are selected as the second electrode group to stimulate the nerve fibers. To avoid the problem of signal distortion, the processing unit arranges the second electrode group (5, 6, 7, 8) in the cycle 3.

Thereafter, the processing unit arranges to generate a stimulation signal corresponding to the band having the spectral peak marked by the circle 3. Since the waveform in this band covers an area smaller than a preset percentage, four electrodes 6, 7, 8 and 9 are selected as the third electrode group to stimulate the nerve fibers. Since the third electrode group (6, 7, 8, 9) satisfies the rule of spacing from another electrode group by at least one electrode in the cycle 1, the third electrode group (6, 7, 8, 9) is arranged in the cycle 1.

Then, the processing unit arranges to generate a stimulation signal corresponding to the band having the spectral peak marked by the circle 4. Since the waveform in this band covers an area smaller than a preset percentage, four electrodes 1, 2, 3 and 4 are selected as the fourth electrode group to stimulate the nerve fibers. To avoid the spatial interaction effect and the temporal interaction effect, the fourth electrode group (1, 2, 3, 4) is arranged in the cycle 5.

Then, the processing unit arranges to generate a stimulation signal corresponding to the band having the spectral peak marked by the circle 5. Since the wave form in this band covers an area larger than a preset percentage, two electrodes 12, 13 are selected as the fifth electrode group to stimulate the nerve fibers. To avoid the spatial interaction effect and the temporal interaction effect, and since at most two electrode groups can be arranged in one single cycle, the fifth electrode group (12, 13) is arranged in the cycle 2. This two electrode groups rule is applicable to sixteen or less electrode apparatus. For apparatus with more electrodes such as twenty two or more, more electrode group can be turned on in the same cycle.

Then, the processing unit arranges to generate a stimulation signal corresponding to the band having the spectral peak marked by the circle 6. Since the waveform in this band covers an area smaller than a preset percentage, four electrodes 3, 4, 5 and 6 are selected as the sixth electrode group to stimulate the nerve fibers. To avoid the problem of signal distortion, the sixth electrode group (3, 4, 5, 6) is arranged in the cycle 7.

Then, the processing unit arranges to generate a stimulation signal corresponding to the band having the spectral peak marked by the circle 7. Since the waveform in this band covers an area smaller than a preset percentage, four electrodes 7, 8, 9 and 10 are selected as the seventh electrode group to stimulate the nerve fibers. To avoid the problem of signal distortion, the seventh electrode group (7, 8, 9, 10) is arranged in the cycle 5.

Then, the processing unit arranges to generate a stimulation signal corresponding to the band having the spectral peak marked by the circle 8. Since the wave form in this band covers an area larger than a preset percentage, two electrodes 0, 1 are selected as the eighth electrode group to stimulate the nerve fibers. To avoid the spatial interaction effect and the temporal interaction effect, and since at most two electrode groups can be arranged in one single cycle, the eighth electrode group (0, 1) is arranged in the cycle 2.

Then, the processing unit arranges to generate a stimulation signal corresponding to the band having the spectral peak marked by the circle 9. Since the waveform in this band covers an area smaller than a preset percentage, four electrodes 0, 1, 2 and 3 are selected as the ninth electrode group to stimulate the nerve fibers. Since only eight cycles are set for presenting the sound signal received by the microphone, and the ninth electrode group (0, 1, 2, 3) could not be arranged in any of the available eight cycles, the processing unit discretionarily selects not to generate a stimulation signal corresponding to the band having the spectral peak marked by the circle 9.

Then, the processing unit arranges to generate a stimulation signal corresponding to the band having the spectral peak marked by the circle 10. Since the wave form in this band covers an area smaller than a preset percentage, four electrodes 12, 13, 14 and 15 are selected as the tenth electrode group to stimulate the nerve fibers. To avoid the spatial interaction effect and the temporal interaction effect, the tenth electrode group (12, 13, 14, 15) is arranged in the cycle 7.

Then, the processing unit arranges to generate a stimulation signal corresponding to the band having the spectral peak marked by the circle 11. Since the waveform in this band covers an area smaller than a preset percentage, four electrodes 4, 5, 6 and 7 are selected as the eleventh electrode group to stimulate the nerve fibers. Since only eight cycles are set for presenting the sound signal received by the microphone, and the eleventh electrode group (4, 5, 6, 7) could not be arranged in any of the available eight cycles, the processing unit discretionarily selects not to generate a stimulation signal corresponding to the band having the spectral peak marked by the circle 11.

Then, the processing unit arranges to generate a stimulation signal corresponding to the band having the spectral peak marked by the circle 12. Since the waveform in this band covers an area smaller than a preset percentage, four electrodes 9, 10, 11 and 12 are selected as the twelfth electrode group to stimulate the nerve fibers. Since only eight cycles are set for presenting the sound signal received by the microphone, and the twelfth electrode group (9, 10, 11, 12) could not be arranged in any of the available eight cycles, the processing unit discretionarily selects not to generate a stimulation signal corresponding to the band having the spectral peak marked by the circle 12.

Then, the processing unit arranges to generate a stimulation signal corresponding to the band having the spectral peak marked by the circle 13. Since the waveform in this band covers an area smaller than a preset percentage, four electrodes 10, 11, 12 and 13 are selected as the thirteenth electrode group to stimulate the nerve fibers. Since only eight cycles are set for presenting the sound signal received by the microphone, and the thirteenth electrode group (10, 11, 12, 13) could not be arranged in any of the available eight cycles, the processing unit discretionarily selects not to generate a stimulation signal corresponding to the band having the spectral peak marked by the circle 13.

Then, the processing unit arranges to generate a stimulation signal corresponding to the band having the spectral peak marked by the circle 14. Since the waveform in this band covers an area smaller than a preset percentage, four electrodes 7, 8, 9 and 10 are selected as the fourteenth electrode group to stimulate the nerve fibers. Since only eight cycles are set for presenting the sound signal received by the microphone, and the thirteenth electrode group (10, 11, 12, 13) could not be arranged in any of the available eight cycles, the processing unit discretionarily selects not to generate a stimulation signal corresponding to the band having the spectral peak marked by the circle 14.

Then, the processing unit arranges to generate a stimulation signal corresponding to the band having the spectral peak marked by the circle 15. Since the wave form in this band covers an area larger than a preset percentage, two electrodes 14, 15 are selected as the fifteenth electrode group to stimulate the nerve fibers. To avoid the spatial interaction effect and the temporal interaction effect, and since at most two electrode groups can be arranged in one single cycle, the fifteenth electrode group (14, 15) is arranged in the cycle 4.

According to the electrical stimulation apparatus and method of the present invention, multiple cycles can be set to present a sound signal approximate to the originally input sound signal. When the number of the cycles having been set is higher, the electrical stimulation apparatus to stimulate nerve fibers can present a sound signal more approximate to the originally input sound signal. Even if the number of the cycles is not high, the electrical stimulation apparatus of the present invention can still transmit the most important frequency components in the received sound signal at the first priority.

The present invention is advantageous in that different quantities of electrodes can be used to form virtual channels. For example, in FIG. 6, four electrodes 5, 6, 7 and 8 are used to generate the stimulation signal simulating the signal frequency having the next highest energy intensity; and two electrodes 3 and 4 are used to generate the stimulation signal simulating the signal frequency having the highest energy intensity. When more electrodes are turned on at the same time, the virtual channel so formed would be narrower. That is, the stimulated nerve corresponds to a narrower range of frequency, and can therefore correspond to a specific frequency, allowing the patient to clearly recognize the sound with the specific frequency. In this manner, the number of electrodes to be selected for use can be determined according to the frequency distribution in different bands, and the sound signal spectrum generated can be more closely approximate to the originally received sound signal spectrum.

Figure 8:
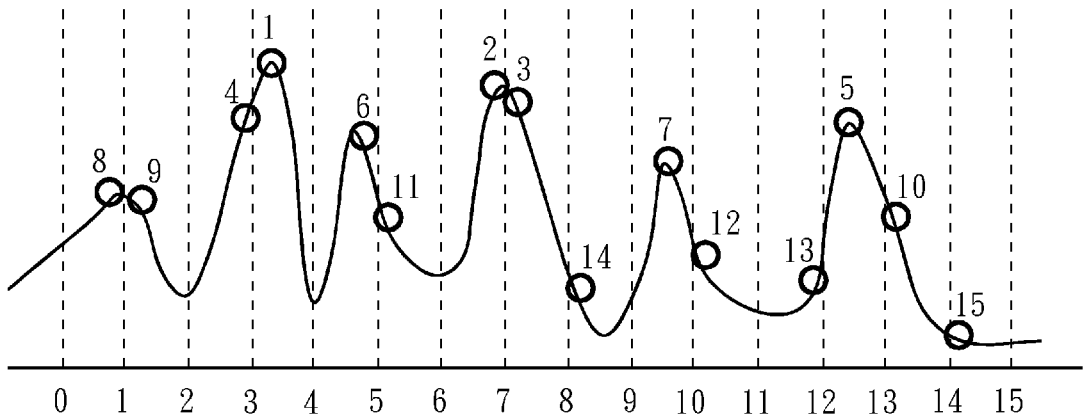
FIG. 8 shows the flow process in a second embodiment of the electrical stimulation method according to the present invention.

Please refer to FIG. 8 that shows the flow process in a second embodiment of the electrical stimulation method according to the present invention. In the second embodiment, total 16 electrodes are provided and denoted by 0, 1, 2 . . . , and 15, respectively. Every electrode corresponds to a center frequency. The center frequencies of any two adjacent electrodes constitute a band of frequencies and therefore, total 15 bands are formed. By driving the 16 electrodes to stimulate nerve fibers, it is possible to reproduce the sound signal as received originally by the receiving unit, which can be a microphone. In the illustrated second embodiment, the sound signal is divided into 15 frequency bands. The processing unit extracts a spectral peak from each of the 15 bands (in FIG. 8, these spectral peaks are separately circled and marked from 1 to 15), so as to determine the stimulation sequence of the bands. In FIG. 8, the higher the spectral peak is, the higher the energy intensity corresponding to the frequency will be. Therefore, in the electrical stimulation apparatus and method of the present invention, the signals with higher energy intensities will be processed first, so that the user can get the most important frequency components in the sound signal.

To avoid the temporal interaction effect from occurring between the stimulation signals corresponding to different bands, in the second embodiment of the present invention, different electrodes are driven in every two cycles. As can be seen FIG. 8, in the second embodiment of the present invention, the electrode groups are arranged only in odd cycles, and the number of electrode groups that can be arranged in each of the odd cycles is not specifically limited. Since the manner of determining the number of electrodes in each electrode group for generating stimulation signal corresponding to each specific band is the same as that in the first embodiment, it is not repeatedly discussed herein.

In the sound signal received by the microphone, since the band having the spectral peak marked by the circle 1 has the largest energy value, the processing unit arranges the first electrode group (3, 4) in the cycle 1 to generate a stimulation signal corresponding to this band. Since the waveform in this band covers an area larger than a preset percentage, two electrodes 3, 4 as the first electrode group are selected to stimulate the nerve fibers.

Then, the processing unit arranges to generate a stimulation signal corresponding to the band having the spectral peak marked by the circle 2. Since the waveform in this band covers an area smaller than a preset percentage, four electrodes 5, 6, 7, and 8 are selected as the second electrode group to stimulate the nerve fibers. To avoid the problem of signal distortion due to spatial and temporal interaction, the processing unit arranges the second electrode group (5, 6, 7, 8) in the cycle 3.

Thereafter, the processing unit arranges to generate a stimulation signal corresponding to the band having the spectral peak marked by the circle 3. Since the waveform in this band covers an area smaller than a preset percentage, four electrodes 6, 7, 8 and 9 are selected as the third electrode group to stimulate the nerve fibers. Since the third electrode group (6, 7, 8, 9) satisfies the rule of spacing from another electrode group by at least one electrode in the cycle 1, the third electrode group (6, 7, 8, 9) is arranged in the cycle 1.

Then, the processing unit arranges to generate a stimulation signal corresponding to the band having the spectral peak marked by the circle 4. Since the waveform in this band covers an area smaller than a preset percentage, four electrodes 1, 2, 3 and 4 are selected as the fourth electrode group to stimulate the nerve fibers. To avoid the spatial and temporal interaction effect, the fourth electrode group (1, 2, 3, 4) is arranged in the cycle 5.

Then, the processing unit arranges to generate a stimulation signal corresponding to the band having the spectral peak marked by the circle 5. Since the wave form in this band covers an area larger than a preset percentage, two electrodes 12, 13 are selected as the fifth electrode group to stimulate the nerve fibers. And, since the fifth electrode group (12, 13) satisfies the rule of spacing from another electrode group by at least one electrode in the cycle 1, the fifth electrode group (12, 13) is arranged in the cycle 1.

Then, the processing unit arranges to generate a stimulation signal corresponding to the band having the spectral peak marked by the circle 6. Since the waveform in this band covers an area smaller than a preset percentage, four electrodes 3, 4, 5 and 6 are selected as the sixth electrode group to stimulate the nerve fibers. To avoid the spatial and temporal interaction effect, the sixth electrode group (3, 4, 5, 6) is arranged in the cycle 7.

Then, the processing unit arranges to generate a stimulation signal corresponding to the band having the spectral peak marked by the circle 7. Since the waveform in this band covers an area smaller than a preset percentage, four electrodes 8, 9, 10 and 11 are selected as the seventh electrode group to stimulate the nerve fibers. To avoid the spatial and temporal interaction effect, the seventh electrode group (8, 9, 10, 11) is arranged in the cycle 5.

Then, the processing unit arranges to generate a stimulation signal corresponding to the band having the spectral peak marked by the circle 8. Since the wave form in this band covers an area larger than a preset percentage, two electrodes 0, 1 are selected as the eighth electrode group to stimulate the nerve fibers. Since the eighth electrode group (0, 1) satisfies the rule of spacing from another electrode group by at least one electrode in the cycle 1, the fifth electrode group (0, 1) is arranged in the cycle 1 also to avoid temporal interaction.

Then, the processing unit arranges to generate a stimulation signal corresponding to the band having the spectral peak marked by the circle 9. Since the waveform in this band covers an area smaller than a preset percentage, four electrodes 0, 1, 2 and 3 are selected as the ninth electrode group to stimulate the nerve fibers. To avoid the spatial and temporal interaction effect, the ninth electrode group (0, 1, 2, 3) is arranged in the cycle 3.

Then, the processing unit arranges to generate a stimulation signal corresponding to the band having the spectral peak marked by the circle 10. Since the wave form in this band covers an area smaller than a preset percentage, four electrodes 12, 13, 14 and 15 are selected as the tenth electrode group to stimulate the nerve fibers. Since the tenth electrode group (12, 13, 14, 15) satisfies the rule of spacing from another electrode group by at least one electrode in the cycle 3, the tenth electrode group (12, 13, 14, 15) is arranged in the cycle 3 also to avoid temporal interaction.

Then, the processing unit arranges to generate a stimulation signal corresponding to the band having the spectral peak marked by the circle 11. Since the waveform in this band covers an area smaller than a preset percentage, four electrodes 4, 5, 6 and 7 are selected as the eleventh electrode group to stimulate the nerve fibers. Since only eight cycles are set for presenting the sound signal received by the microphone, and the eleventh electrode group (4, 5, 6, 7) could not be arranged in any of the available eight cycles, the processing unit discretionarily selects not to generate a stimulation signal corresponding to the band having the spectral peak marked by the circle 11.

Then, the processing unit arranges to generate a stimulation signal corresponding to the band having the spectral peak marked by the circle 12. Since the waveform in this band covers an area smaller than a preset percentage, four electrodes 9, 10, 11 and 12 are selected as the twelfth electrode group to stimulate the nerve fibers. To avoid the spatial and temporal interaction effect, the twelfth electrode group (9, 10, 11, 12) is arranged in the cycle 7.

Then, the processing unit arranges to generate a stimulation signal corresponding to the band having the spectral peak marked by the circle 13. Since the waveform in this band covers an area smaller than a preset percentage, four electrodes 10, 11, 12 and 13 are selected as the thirteenth electrode group to stimulate the nerve fibers. Since only eight cycles are set for presenting the sound signal received by the microphone, and the thirteenth electrode group (10, 11, 12, 13) could not be arranged in any of the available eight cycles, the processing unit discretionarily selects not to generate a stimulation signal corresponding to the band having the spectral peak marked by the circle 13.

Then, the processing unit arranges to generate a stimulation signal corresponding to the band having the spectral peak marked by the circle 14. Since the waveform in this band covers an area smaller than a preset percentage, four electrodes 7, 8, 9 and 10 are selected as the fourteenth electrode group to stimulate the nerve fibers. Since only eight cycles are set for presenting the sound signal received by the microphone, and the thirteenth electrode group (10, 11, 12, 13) could not be arranged in any of the available eight cycles, the processing unit discretionarily selects not to generate a stimulation signal corresponding to the band having the spectral peak marked by the circle 14.

Then, the processing unit arranges to generate a stimulation signal corresponding to the band having the spectral peak marked by the circle 15. Since the wave form in this band covers an area larger than a preset percentage, two electrodes 14, 15 are selected as the fifteenth electrode group to stimulate the nerve fibers. Since the fifteenth electrode group (14, 15) satisfies the rule of spacing from another electrode group by at least one electrode in the cycle 5, the fifteenth electrode group (14, 15) is arranged in the cycle 5 also to avoid temporal interaction.

As can be seen from the above-described two embodiments, it is understood the present invention arranges different numbers of electrode groups to form virtual channels according to the frequency distribution in each of the bands, and can therefore present simulated signal more approximate to the originally input sound signal. In addition, the number of the electrodes disclosed in this embodiment (2 and 4) is for the example but not the limitation. Users with general knowledge in this field should be able to easily apply to different number of the electrodes. Further, the present invention successfully reduces the number of cycles of stimulation signals, compared to the prior art electrode stimulation techniques.

The present invention has been described with some preferred embodiments thereof and it is understood that many changes and modifications in the described embodiments can be carried out without departing from the scope and the spirit of the invention that is intended to be limited only by the appended claims.

What is claimed is:

1. An electrical stimulation method to stimulate nerve fibers, comprising the following steps of:
   receiving a sound signal by a receiving unit;
   dividing the received sound signal into a plurality of frequency bands by a processing unit;
   extracting a spectral peak from each of the frequency bands and determining a stimulation sequence of each frequency bands based on the spectral peaks by the processing unit;
   selectively driving a plurality of electrode groups in a plurality of cycles based on the stimulation sequence of each frequency band and a determination rule by the processing unit, so that a plurality of stimulation signals corresponding to each of the frequency bands are generated for stimulating nerve fibers; and the determination rule comprising disposing at least one electrode between each of the electrode groups in each of the cycles, avoiding the electrode groups driven in two adjacent ones of the plural cycles from repeatedly using the same electrodes, and disposing at least one electrode between each of the electrode groups in two adjacent ones of the plural cycles;
   presenting the sound signal through the plurality of stimulation signals; and
   wherein, two or more of the plurality of electrode groups are stimulated in at least a single one of the plurality of cycles;
   wherein, all of the stimulated plurality of electrode groups in each cycle are stimulated only when the processing unit follows the determination rule.

2. The electrical stimulation method to stimulate nerve fibers as claimed in claim 1, wherein the processing unit drives the plurality of electrode groups in interval of cycles and the electrode groups to be driven are spaced from each other by at least one electrode.

3. The electrical stimulation method to stimulate nerve fibers as claimed in claim 1, wherein the electrode groups having different numbers of electrodes are driven by the processing unit in each of the plurality of cycles.

4. The electrical stimulation method to stimulate nerve fibers as claimed in claim 1, wherein each of the electrode groups comprises two or more adjacent electrodes.

5. The electrical stimulation method to stimulate nerve fibers as claimed in claim 1, wherein the plurality of frequency bands is produced when the sound signal is analyzed by fast Fourier transform (FFT) or other frequency spectrum analyzing method or the sound signal is passing through a plurality of band-pass filters.

6. The electrical stimulation method to stimulate nerve fibers as claimed in claim 1, further comprising the step of analyzing the sound signal to obtain a relationship between frequency and energy intensity of the sound signal by the processing unit.

7. The electrical stimulation method to stimulate nerve fibers as claimed in claim 1, wherein when the spectral peak has the highest value, energy intensity corresponding to the spectral peak has the highest value.

8. The electrical stimulation method to stimulate nerve fibers as claimed in claim 7, wherein when the spectral peak value has the highest value, the processing unit drives the electrodes at the first priority to generate the stimulation signal corresponding to the frequency band.

9. The electrical stimulation method to stimulate nerve fibers as claimed in claim 1, wherein an amount of current for driving each of the electrode groups is determined based on the spectral peak of the frequency band to which the electrode group corresponds.

10. An electrical stimulation apparatus to stimulate nerve fibers, comprising:
    a micro-electrode array including a plurality of electrodes, and the electrodes respectively corresponding to a different center frequency after the electrodes are driven;
    a receiving unit for receiving a sound signal; and
    a processing unit for dividing the received sound signal into a plurality of frequency bands, extracting a spectral peak from each of the frequency bands, and determining a stimulation sequence of each frequency bands based on the spectral peaks; the processing unit selectively driving a plurality of electrode groups in a plurality of cycles based on the stimulation sequence of each frequency band and a determination rule, so that a plurality of stimulation signals corresponding to each of the frequency bands are generated for stimulating nerve fibers and the sound signal is presented through the plurality of stimulation signals;

wherein the determination rule comprising disposing at least one electrode between each of the electrode groups in each of the cycles, avoiding the electrode driven in the continuous cycles, or avoiding the electrode groups in two adjacent ones of the plural cycles from repeatedly using the same electrodes, and disposing at least one electrode between each of the electrode groups in two adjacent ones of the plural cycles;

wherein, two or more of the plurality of electrode groups are stimulated in at least a single one of the plurality of cycles;

wherein, all of the stimulated plurality of electrode groups in each cycle are stimulated only when the processing unit follows the determination rule.

11. The electrical stimulation apparatus to stimulate nerve fibers as claimed in claim 10, wherein the processing unit drives the plurality of electrode groups in interval of cycles and the electrode groups to be driven are spaced from each other by at least one electrode.

12. The electrical stimulation apparatus to stimulate nerve fibers as claimed in claim 10, wherein the electrode groups having different numbers of electrodes are driven by the processing unit in each of the plurality of cycles.

13. The electrical stimulation apparatus to stimulate nerve fibers as claimed in claim 10, wherein each of the electrode groups comprises two or more adjacent electrodes.

14. The electrical stimulation apparatus to stimulate nerve fibers as claimed in claim 10, wherein the plurality of frequency bands is produced when the sound signal is analyzed by fast Fourier transform (FFT) or other frequency spectrum analyzing method or the sound signal is passing through a plurality of band-pass filters.

15. The electrical stimulation apparatus to stimulate nerve fibers as claimed in claim 10, wherein the processing unit analyzes the sound signal to obtain a relationship between frequency and energy intensity in the sound signal.

16. The electrical stimulation apparatus to stimulate nerve fibers as claimed in claim 10, wherein when the spectral peak has the highest value, energy intensity corresponding to the spectral peak has the highest value.

17. The electrical stimulation apparatus to stimulate nerve fibers as claimed in claim 16, wherein when the spectral peak value has the highest value, the processing unit drives the electrodes at the first priority to generate the stimulation signal corresponding to the frequency band.

18. The electrical stimulation apparatus to stimulate nerve fibers as claimed in claim 10, wherein an amount of current for driving each of the electrode groups is determined based on the spectral peak of the frequency band to which the electrode group corresponds.

* * * * *